US00PP24091P3

(12) United States Plant Patent
Leis et al.

(10) Patent No.: US PP24,091 P3
(45) Date of Patent: Dec. 17, 2013

(54) APPLE TREE NAMED 'GEMINI'

(50) Latin Name: *Malus domestica Mill.*
Varietal Denomination: Gemini

(75) Inventors: Michelangelo Leis, Ferrara (IT); Alessio Martinelli, Ferrara (IT); Francesco Tagliani, Argenta (IT); Gianfranco Castagnoli, Quingentole (IT); Donata Azzolini, legal representative, Quingentole (IT); Pietro Castagnoli, legal representative, Quingentole (IT); Alessandro Castagnoli, legal representative, Quingentole (IT)

(73) Assignee: C.I.V.—Consorzio Italiano Vivaisti—Societa Consortile A R.L., Comacchio FE (IT)

( * ) Notice: Subject to any disclaimer, the term of this patent is extended or adjusted under 35 U.S.C. 154(b) by 26 days.

(21) Appl. No.: 13/374,436

(22) Filed: Dec. 29, 2011

(65) Prior Publication Data

US 2013/0031682 P1 Jan. 31, 2013

(30) Foreign Application Priority Data

Jul. 26, 2011 (QZ) ..... PBR 20111878

(51) Int. Cl.
*A01H 5/00* (2006.01)

(52) U.S. Cl.
USPC ..... Plt./161

(58) Field of Classification Search
USPC ..... Plt./172, 161
See application file for complete search history.

*Primary Examiner* — Kent L Bell
(74) *Attorney, Agent, or Firm* — Foley & Lardner LLP

(57) ABSTRACT

A new and distinct *Malus domestica Mill.* apple tree variety named 'Gemini' particularly characterized by medium vigorous tree with spreading habit. Highly productive with precocious fruit bearing. Resistant to scab, very low susceptibility to powdery mildew. The fruit is very attractive, big, larger than 'Gala' with a regular conical shape. The ground color is green with a uniform brilliant ruby red blush, the area of over color is very large. Not subject to cracking. The flesh is creamy, crispy, fresh and juicy with a slight acidity taste. The storage life is comparable to 'Gala'.

4 Drawing Sheets

Latin name of the genus and species of the plant claimed: *Malus domestica Mill.*

Variety denomination: 'Gemini'.

PRIORITY CLAIM

This application claims the benefit of European Community Plant Variety Office Plant Breeders' Rights Application No. 2011/1878, filed Jul. 26, 2011.

BACKGROUND OF THE INVENTION

The present invention relates to a new and distinct variety of apple tree, botanically known as *Malus domestica Mill.* of the Family Rosaceae, and hereinafter referred to by the variety denomination 'Gemini'.

The new *Malus* variety is a product of a planned breeding program conducted by the inventors, Michelangelo Leis, Alessio Martinelli, Gianfranco Castagnoli and Francesco Tagliani in S. Giuseppe di Comacchio (Ferrara), Italy. The objective of the breeding program was to develop new *Malus* varieties with improved production characteristics, high-quality flavour and aroma, and sustainability by increasing the tree's natural resistance. The primary objective of the research programme is to selection new apple varieties with natural resistances, in particular to scab.

The new *Malus* variety, 'Gemini', originated from a cross made in a planned, controlled breeding program in S. Giuseppe di Comacchio (Ferrara), Italy. The female parent is the 'Gala' variety. The male parent is an unpatented selection denominated 'A3-7'. 'Gemini' was discovered and selected in September 2004 by the inventors as a flowering plant within the progeny of the stated cross in a controlled environment in S. Giuseppe di Comacchio (Ferrara), Italy.

Asexual reproduction of the new *Malus* variety by budding and grafting was first performed in September 2004 and in the following years in S. Giuseppe di Comacchio (Ferrara), Italy, and has demonstrated that the combination of characteristics as herein disclosed for the new *Malus* variety are firmly fixed and retained through successive generations of asexual reproduction. The new variety reproduces true to type.

In comparison to its parents, 'Gemini' differs primarily in the traits listed in Table 1.

TABLE 1

| Comparison with parent varieties | | | |
|---|---|---|---|
| Characteristic in which the variety is different | State of expression of candidate variety | The female parent (Gala) | The male parent (A3-7) |
| Resistance to scab | Yes | No | Yes |
| Fruit: relative area of over color | Very large | Medium | Medium to large |
| Fruit: over color | Ruby red | Red | Medium red |
| Fruit: pattern of over color | Only solid flush | Solid flush with defined stripes | Only solid flush |
| Fruit: size | Large | Medium | Medium to large |
| Time of eating maturity | Medium to late | Medium | Medium to late |

BRIEF DESCRIPTION OF THE INVENTION

The following traits have been repeatedly observed and are determined to be unique characteristics of 'Gemini' which in combination distinguish this apple tree as a new and distinct variety:

1. Intense ruby red color;
2. Scab resistance;
3. Medium vigor, open habit with short branches;
4. High sugar content and
5. Good storage ability.

In comparison to the similar variety 'Galaxy', 'Gemini' differs primarily in the traits listed in Table 2:

TABLE 2

Comparison with Similar Variety:

| Denomination of similar variety | Characteristic in which the similar variety is different | State of expression of similar variety | State of expression of candidate variety |
|---|---|---|---|
| 'Galaxy' | Relative area of over color | Medium | Very large |
| | Pattern of over color | Solid flush with defined stripes | Only solid flush |
| | Resistance to disease | No | Scab resistant |

Of the commercial cultivars known to the inventors, the most similar in comparison to 'Gemini' is the variety 'Galaxy' as compared in Table 2.

BRIEF DESCRIPTION OF THE DRAWINGS

The accompanying photographs illustrate the overall appearance of the new apple tree 'Gemini' showing the colors as true as is reasonably possible with color reproductions of this type. Color in the photographs may differ slightly from the color value cited in the detailed botanical description, which accurately describe the color of 'Gemini'.

DETAILED BOTANICAL DESCRIPTION

Figure 1:
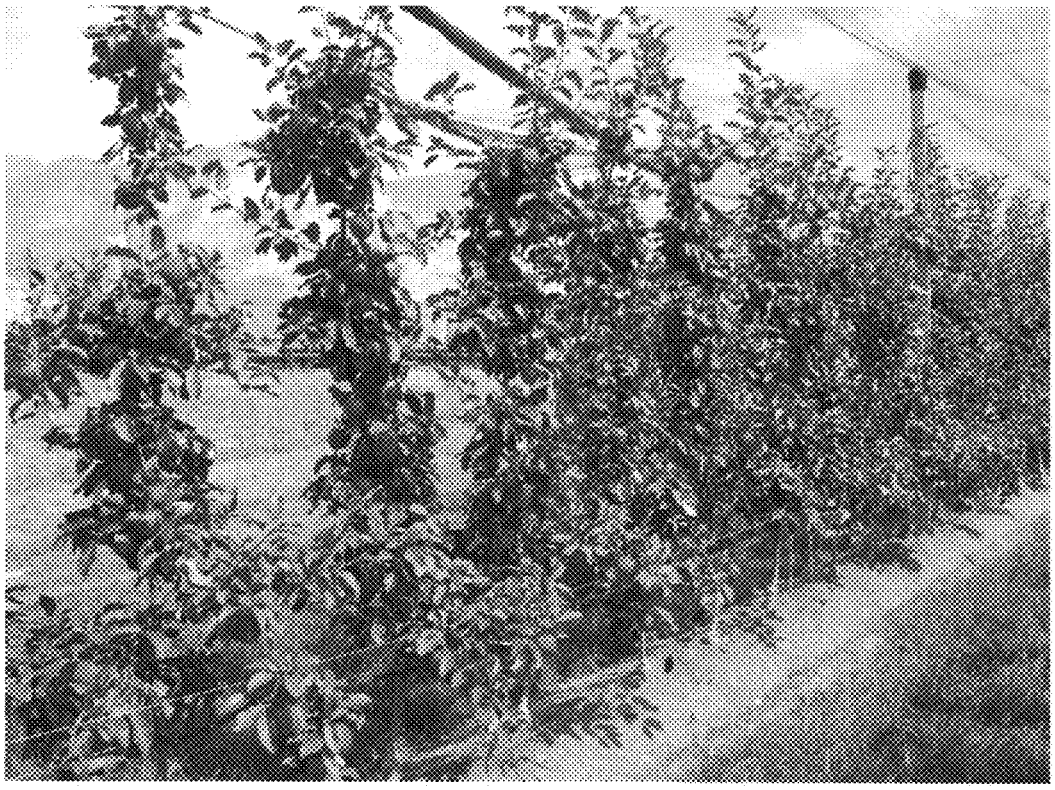
FIG. 1: illustrates the tree of 'Gemini'.
Figure 2:
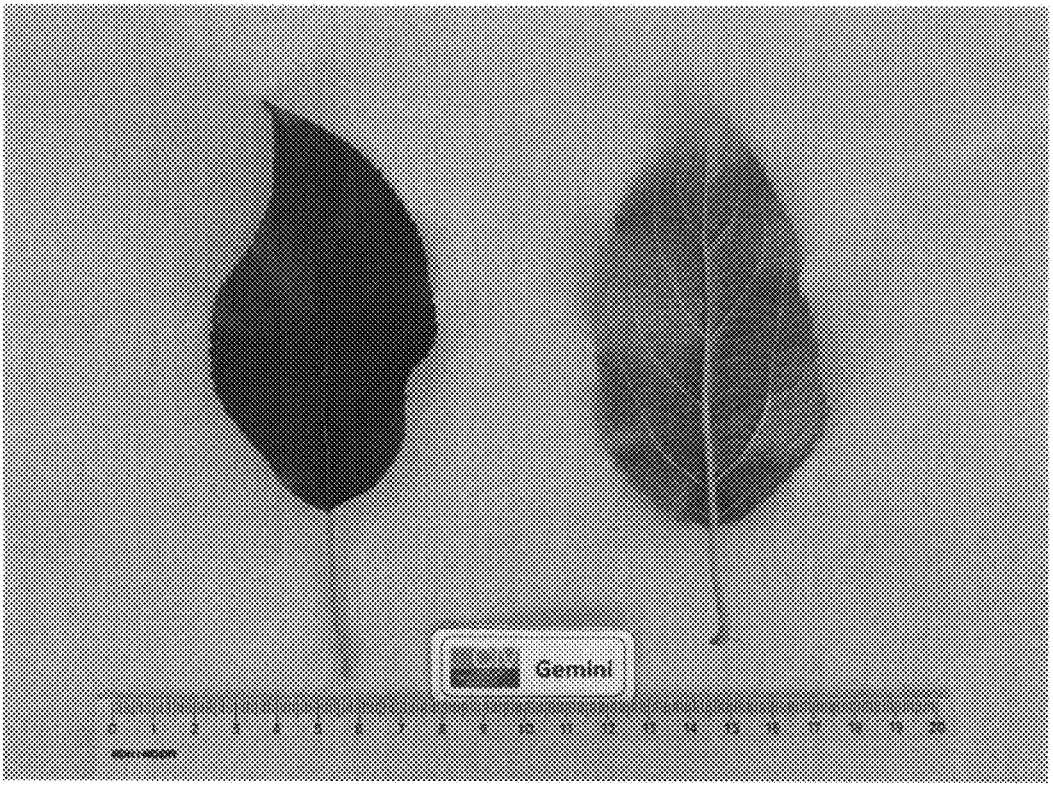
FIG. 2: illustrates the leaves of 'Gemini'.
Figure 3:
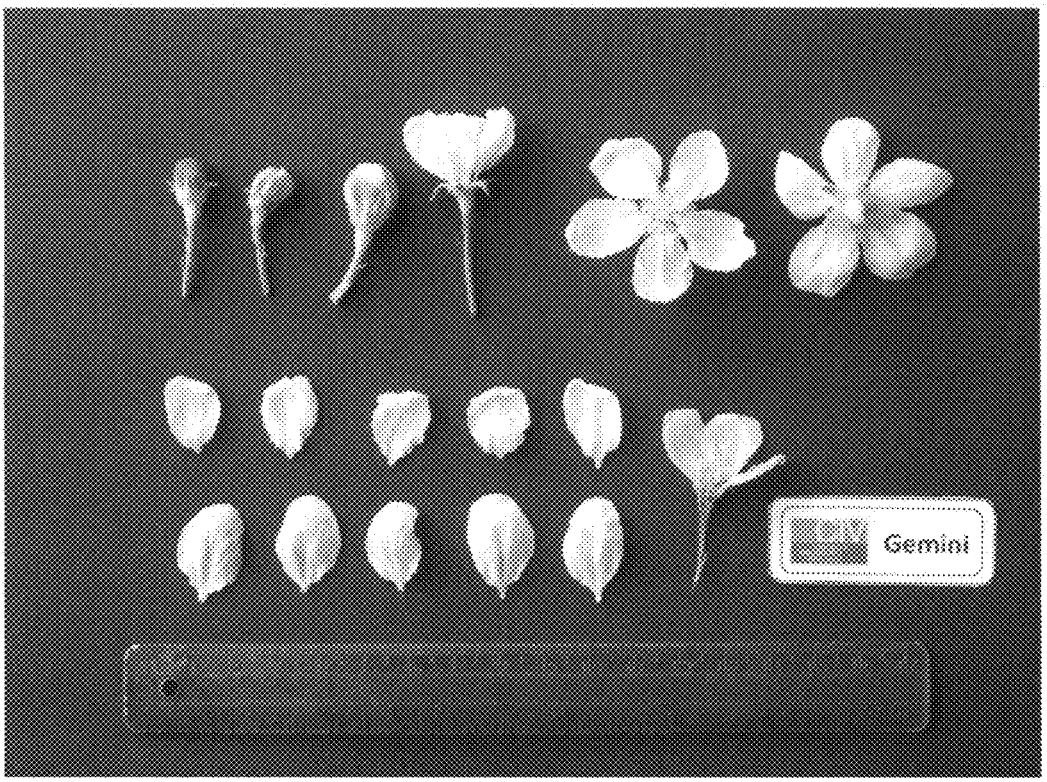
FIG. 3: illustrates the flowers of 'Gemini
Figure 4:
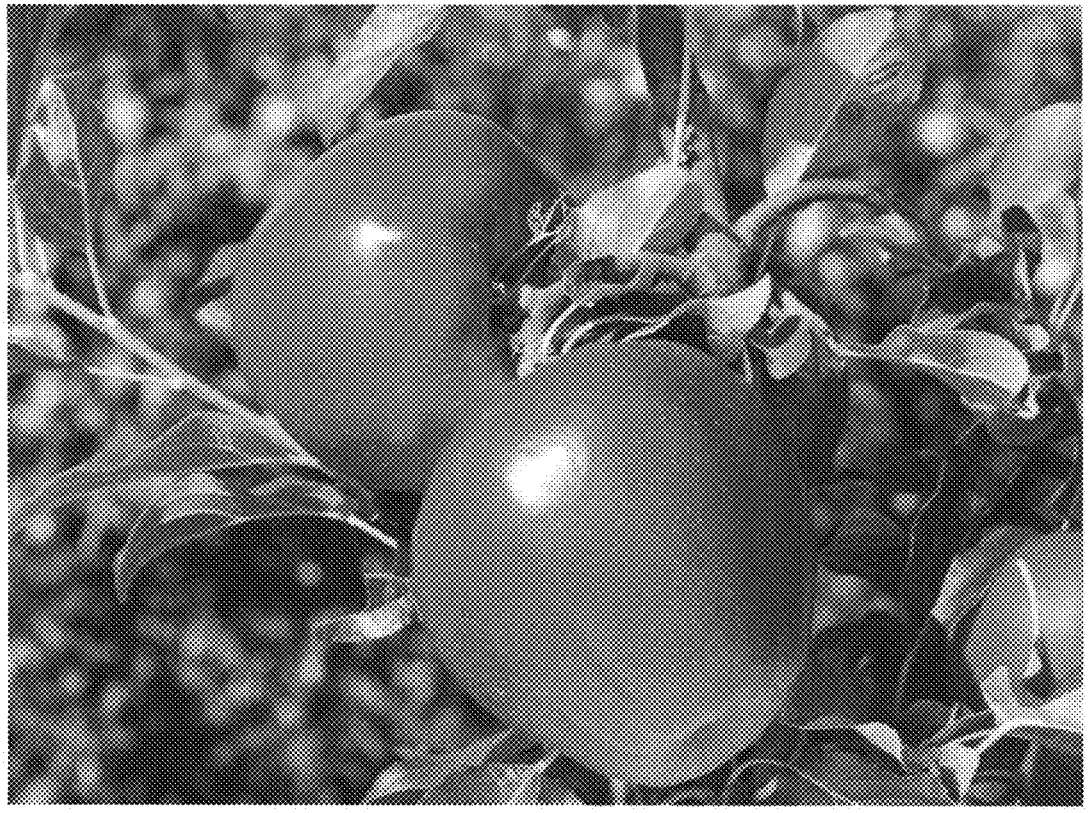
' and
FIG. 4: illustrates the fruits of 'Gemini'.

The new *Malus* variety 'Gemini' has not been observed under all possible environmental conditions. The phenotype of the new variety may vary with variations in environment such as temperature, light intensity, and day length without any change in the genotype of the tree.

The aforementioned photographs, together with the following observations, measurements and values describe the new *Malus* variety 'Gemini' as grown in the apple farm in S. Giuseppe di Comacchio (Ferrara), Italy, under conditions which closely approximate those generally used in commercial practice. The apple farm where 'Gemini' is grown is situated near the Adriatic sea (44°45' North, 12°11' East) and is zero (0) meters above sea level. The soil of the apple farm where 'Gemini' is grown is sandy, and the soil is treated with manure every year and irrigated with drip irrigation systems. The climate is temperate continental with high summer temperatures and low winter temperatures.

Unless otherwise stated, the detailed botanical description includes observations, measurements and values based on four (4) year old 'Gemini' trees that were grown in the apple farm in S. Giuseppe di Comacchio (Ferrara), Italy, from 2007 to 2010 All trees were of cropping maturity. Quantified measurements are expressed as an average of measurements taken from a number of individual trees of 'Gemini'. The measurements of any individual tree, or any group of trees, of the new variety may vary from the stated average.

Color references are made to The Royal Horticultural Society Colour Chart (R.H.S.), except where general colors of ordinary significance are used. Color values were taken under daylight conditions at approximately 10:00 am in S. Giuseppe di Comacchio (Ferrara), Italy.

All trees of 'Gemini', insofar as they have been observed, have been identical in all the characteristics described below.

Classification:

*Botanical.—Malus domestica Mill.*

Parentage:

*Female parent.—Malus domestica Mill.* 'Gala'.

*Male parent.—Malus domestica Mill.* 'A3-7' (unpatented selection).

Propagation: Budding and grafting on M9 rootstock.

Tree:

*Age.*—Observed plants were four years old.

*Vigor.*—Medium vigor.

*Tree type.*—Ramified.

*Habit.*—Spreading, branches angle is typically 45 to 75 degrees from the vertical. stem.

*Density.*—Medium density.

*Cropping behavior.*—Precocious fruit bearing with high productivity.

*Type of bearing.*—Typically long shoot, presence of spur on 2-3 year old branches.

*Production.*—$4^{th}$ year: 16 Kg.

*Size.*—Height: 2.8 m. Spread: 1.30 m. Trunk Diameter: about 35 mm as measured 20 cm above point of grafting.

*Surface texture.*—Smooth.

*Bark color.*—Brown, RHS 166 A.

*Trunk lenticels.*—

*Overall shape.*—Round to elongated. Length: 1.6 mm. Width: 1.5 mm. Color: Yellow-brown RHS 164 C. Density: 3 to 4 per $cm^2$.

*Branches.*—Number per tree: about 20 at four (4) years. Length: Varies due to pyramidal shape of tree. At four (4) years, maximum of 90 cm to 110 cm; minimum of 30 cm to 50 cm. Diameter (at 3 years): About 10 mm to 14 mm. Surface texture: smooth. Color (at 3 years): grey, RHS 201 A. Internode length: About 2.5 cm to 3.5 cm. Internode diameter: About 9 mm to 12 mm in the middle of branches.

*Branches lenticels.*—Length: 0.9 mm. Width: 1.2 mm. Color: Yellow-brown, RHS 164 B. Density: About 3 to 4 per $cm^2$.

Leaves:

*Arrangement.*—Alternate, simple, petiolated.

*Lamina.*—Size: Length (4 year old): 98.4 mm (from $3^{rd}$ to $5^{th}$ fully expanded leaf). Width (4 year old): 47.3 mm (from $3^{rd}$ to $5^{th}$ fully expanded leaf).

*Length/width ratio.*—2.08. Overall Shape: elliptical-elongated. Base shape: rounded. Apex shape: acuminate. Margin: serrate. Pubescence: absent on upper surface and weak pubescent on lower surface. Attitude in relation to shoot: outwards. Color (mature leaves): green, RHS 137 A on the upper side and 147 B underside.

*Venation.*—Type: prominent pinnate venation from a midrib to the edge. Color: green, RHS 148 C.

*Petiole.*—Length: about 28 mm. Diameter: about 1.8 mm. Texture: hairy. Color: yellow-green, RHS 146 C with anthocyanin coloration located in a small area on the base, RHS 58A red-purple.

*Stipule.*—Arrangement: adnate, grown together; medium size.

*Distance of stipules from basal attachment of petiole.*—Average 3 mm. Length: 5 mm to 9 mm. Width: 0.6 mm to 1.9 mm.

Spur:

*Present.*—On 2-3 year old shoots.

*Distance between each spur.*—On the two-three year old branches, the distance is about 20 mm to 50 mm.

*Number of fruit per spur.*—2 to 4 without thinning.

Flowers:

*Blooming time.*—Full bloom on April 9$^{th}$ in S. Giuseppe di Comacchio (Ferrara) Italy in year 2011.

*Blooming period.*—8 to 12 days.

*Fragrance.*—Slight.

*Type.*—Inflorescence.

*Number of flowers per inflorescence.*—5 to 6.

*Flower size.*—Diameter: about 44 mm. Flower depth (height of the corolla): about 14-15 mm, measured when the flowers are fully open. Flower color: Primarily white, RHS 155 D, when petals fully opened, undersides of petals there are shades red-purple color, RHS 67 A, In the balloon stage the color is RHS 55A, red.

*Buds.*—Number of buds per spur: typically, one or two on each spur. Shape: pointed. Length: about 7.5 mm. Width: about 4.5 mm. Color: brown, RHS 187 A with hairy surface.

*Petals.*—Arrangement: intermediate. Number per flower: typically five (5). Length: average 20.96 mm. Width: average 14 mm. Length/width ratio: 1.5. Overall shape: elliptic. Apex shape: obtuse. Base shape: rounded. Texture: smooth. Margin: entire. Color (upper surface): white, RHS 155 D. Color (lower surface): white, RHS 155 D with shade red-purple RHS 67 A.

*Sepals.*—Number per flower: five (5). Length: average 5.76 mm. Width: average 3.56 mm. Length/width ratio: 1.62. Overall shape: lanceolate. Apex shape: acute. Texture: hairy. Margin: entire. Color (upper surface): green RHS 138 C. Color (lower surface): green RHS 138 B.

*Pedicel.*—Length: average 25.8 mm. Diameter: 2 to 3 mm. Texture: hairy. Color: green, RHS 138 B.

Fruit:

*Keeping quality.*—The fruit keeps well on the tree. The storage life is comparable to 'Gala'. It has a good shelf life.

*Maturity when described.*—Ripe for eating.

*Maturity period after full bloom.*—About 131 days in S. Giuseppe di Comacchio (Ferrara) Italy.

*Date of first and last pickings.*—About 15 August and 22 August in S. Giuseppe di Comacchio (Ferrara) Italy (North 44°45'46.2", East 012°11'31.9") in year 2011.

*General shape.*—Conic.

*Average weight.*—216.73 g.

*Fruit size.*—Average height: 71.44 mm. Average diameter (at widest point): 81.55 mm.

*Position of maximum diameter.*—Between ¾ of the height near stem end.

*Height/diameter ratio.*—0.88.

*Stem.*—Length: about 23.47 mm. Diameter: 2.62 mm. Color: yellow-green group, RHS 146 C.

*Stalk cavity.*—Depth: average 20.24 mm. Width: average 40.63 mm.

*Eye basin.*—

*Aperture of eye.*—Fully open. Depth: average 8.46 mm. Width: average 29.12 mm. Crowning at calyx end: absent or weak. Position of sepals: erect and converging. Calyx tube: funnel form.

*Skin.*—Thickness: medium. Texture: smooth. Bloom: absent or very low. Greasiness: absent. Firmness (at picking time): 9 to 10 kg/cm$^2$. Overcolor color: red, RHS 46 A. Percentage of skin surface with overcolor color: very large. Pattern of overcolor: only solid flush. Intensity of overcolor: dark. Ground color: yellow-green, RHS 154 B.

*Skin lenticels.*—Shape: round. Length: about 1.0 mm. Width: about 1.0 mm. Color: yellow-white, RHS 158 B. Density: about 3 per cm$^2$ in the central area of the surface of fruit. The number of lenticels increases in a direction toward the hollow of the calyx and the size of the lenticels decreases.

*Flesh.*—Color: yellow-white group , RHS 158 B. Texture: firm, crisp and juicy. Aroma: medium. Eating quality: good with slight acidity taste. Sugar content (at picking time): 12 to 13° Brix. Acidity/Starch (at picking time): 4.5 to 6.5 g/l of Malic acid measured when the starch degradation is 2.5 using the Laimburg scale 1 to 5.

*Core.*—Symmetry of core: slightly asymmetric. Distinctness of core lines: no more evident.

*Locules.*—Number (per fruit): 5 (five). Length: 14.79 mm. Width: 6.72 mm. Form: fully open.

Seeds:

*Number per fruit.*—6 to 14.

*Number per locule.*—About 2 to 3.

*Shape.*—Ellipsoid, elongated and pointed.

*Length.*—Average 8.18 mm.

*Width.*—Average 4.73 mm.

*Color.*—Brown, RHS 200 D.

Reproductive organs:

*Androecium.*—Stamens: Number per flower: about 20 (Twenty). Length: average 7.73 mm. Filament: Length: about 5.9 mm. Color: green-white, RHS 157 B. Anther: Shape: ovoid, flat in the center. Length: 2.35 mm. Diameter: 1.73 mm. Color: yellow, RHS 10 C. Pollen: Amount: abundant. Color: yellow, RHS 13 C. Requirements: the crab apple *Malus* 'Evereste' is a good pollinator.

*Gynoecium.*—Stigma: Shape: funnel shape with receptive surface on top. Length: 1.0 mm. Width: 0.5 mm. Color: yellow, RHS 145 A. Style: Number per flower: 5 (Five). Length: about 10 mm. Width: about 0.3 mm.

Color: yellow-green, RHS 138 B. Ovary: Length: about 4.0 mm. Width: about 3.0 mm. Color: yellow-green, RHS 138 B.

Use: Fresh market.

Sensitivity to disease/pests: Scab resistance.

Winter hardiness: Tolerance to temperatures of −12° C. without observed damage to wood and buds of dormant apple trees; but open flowers and young fruitlets are killed by exposure to −3° C. to −5° C., depending on the length of exposure.

Drought/heat tolerance: Good tolerance to heat, up to 40° C., growth is limited by drought periods without irrigation.

Shipping/storage characteristics: Good storability under ULO-conditions (1° C., 2% $0_2$, 2% $CO_2$) for up to six (6) months.

We claim:

1. A new and distinct *Malus domestica Mill.* apple tree named 'Gemini', substantially as illustrated and described herein.

* * * * *